United States Patent [19]
Powell

[11] 3,933,809

[45] Jan. 20, 1976

[54] 2-(DIHALONITROMETHYL)-5,6-DIHYDRO-4H-1,3-THIAZINES

[75] Inventor: James E. Powell, Modesto, Calif.

[73] Assignee: Shell Oil Company, Houston, Tex.

[22] Filed: Nov. 1, 1974

[21] Appl. No.: 520,191

[52] U.S. Cl............................. 260/243 R; 424/246
[51] Int. Cl.$^2$................................. C07D 279/06
[58] Field of Search ........................... 260/243 R

[56] References Cited
UNITED STATES PATENTS 3,551,417  12/1970  Symon et al. ..................... 260/243

OTHER PUBLICATIONS

Feuer et al., *J. Org. Chem.*, Vol. 37, No. 23, pp. 3662–3670, (1972).

Lawrence, (Ph.D. Thesis), "Preparation of Nitralkyl Heterocyclic Compounds by the Alkyl Nitrate Nitration", Purdue University, June, 1970, Pub. by University Microfilms, Wycomb, England.

*Primary Examiner*—John M. Ford

[57] ABSTRACT

Novel insecticidal 2-(dihalonitromethyl)-5,6-dihydro-4H-1,3-thiazines.

2 Claims, No Drawings

2-(DIHALONITROMETHYL)-5,6-DIHYDRO-4H-1,3-THIAZINES

DESCRIPTION OF THE INVENTION

It has been found that useful insecticidal activity is possessed by 2-(dihalonitromethyl)-5,6-dihydro-4H-1,3-thiazines of the formula

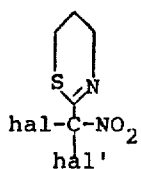

wherein hal represents chlorine, bromine or fluorine, and hal' represents chlorine or bromine.

The preparation of these compounds is illustrated in the following examples. In all cases, the identity of the product, and of any intermediate employed, was confirmed by elemental analysis, and by infrared and nuclear magnetic resonance spectrum analyses.

EXAMPLE 1 —
2-(dichloronitromethyl)-5,6-dihydro-4H-1,3-thiazine (1)

Ethyl nitro(tetrahydro-2H-1,3-thiazin-2-ylidene)-acetate (1B)

To a mixture of 235 g of 5,6-dihydro-2-(methylthio)-4H-1,3-thiazine (A. F. McKay, et al., J. Am. Chem. Soc., 80, 3339 (1958)) and 2 g of zinc chloride, at approximately 115° in a nitrogen atmosphere, 263 g of ethyl nitroacetate (S. Zea, et at., Kogyo Kagaku Zasshi, 74, 70 (1971)) was added dropwise over a 1.5 hour period. The mixture was held at 110°–120°. When evolution of methyl mercaptan ceased after 45 minutes further stirring of the heated mixture, 1 g of zinc chloride was added and the mixture was stirred at about 115° for 1.25 hours. An additional 1 g of zinc chloride then was added and stirring of the mixture at about 115° was continued for 1.5 hours. The mixture then was poured into a cooled solution of 2/1 ether/isopropyl alcohol mixture, The crystallized product was collected, washed with ether and dried under reduced pressure to leave a tan solid, m.p. 100°–102°, which on recrystallization from methanol gave 1B as a pale yellow solid, m.p. 105°–106°.

Tetrahydro-2-(nitromethylene)-2H-1,3-thiazine (1A)

2.3 g of 1B was added to 10 ml of 20% aqueous sodium hydroxide and the mixture was stirred at room temperature for 12 hours. The resulting solution was treated dropwise with 3.5 g of acetic acid. The addition was accompanied by vigorous gas evolution. The resulting mixture was extracted with methylene chloride and the extract was dried (magnesium sulfate) and concentrated under reduced pressure to give 1A as a pale yellow solid, m.p. 76°–78°.

1. A solution of 2.2 g of chlorine in 100 ml of methylene chloride was added dropwise to a solution of 4.8 g of 1A in 25 ml methylene chloride, the mixture being held at 5°–15°. After the addition was complete, 3.1 g of triethylamine, followed by an additional 2,7 g of chlorine in in 100 ml of methylene chloride was added, the mixture being held at 5°–10°. The mixture then was washed with saturated sodium bicarbonate solution and saturated salt solution, dried ($Na_2SO_4$) and concentrated under reduced pressure to give 1, as an amber oil, homogeneous by thin layer chromatography, crystalline at low temperature (melting point below 20°).

EXAMPLE 2 —
2-(bromochloronitromethyl)-5,6-dihydro-4H-1,3-thiazine (2)

2-(bromonitromethylene)-tetrahydro-2H-1,3-thiazine (2A)

A solution of 3.2 g of bromine in 10 ml of methylene chloride was added dropwise to a solution of 3.2 g of 1A in 50 ml of water, the temperature being held at 5°–10°. The mixture was then stirred for 45 minutes when 200 ml of methylene chloride was added to dissolve the solid material. The organic phase was separated, washed with water, dried ($Na_2SO_4$) and concentrated under reduced pressure to give a yellow solid. This was washed with ether to give 2A as a yellow solid, m.p. 122° (with decomposition).

2. A mixture of 7.2 g of 2A and 4.5 g of N-chlorosuccinimide in 110 ml of carbon tetrachloride was stirred at room temperature. After 2 hours stirring, the mixture was filtered and the solid matter was washed with carbon tetrachloride. Concentration of the filtrate plus the washings gave a yellow semisolid. This was chromatographed on silica gel using dry-column technique and a 1:4:10 tetrahydrofuran/ethyl acetate/hexane mixture as eluent. The only mobile (ultra-violet active) component was cut out and extracted with acetone to give a pale yellow liquid which solidified to a slightly mushy solid, m.p., 25°–40°. This was recrystallized from ether-pentane to give 2, as a white solid, m.p., 42.5°–49°.

EXAMPLE 3 —
2-(dibromonitromethyl)-5,6-dihydro-4H-1,3-thiazine (3)

A solution of 8.0 g bromine in 50 ml of chloroform was added dropwise to a solution of 4.0 g of 1A in 100 ml of chloroform, the mixture being held at 5°–10°. After stirring for an additional hour at the same temperature, the mixture was poured into excess saturated sodium bicarbonate solution and extracted with chloroform. The organic extract was washed with salt solution, dried ($Na_2SO_4$) and concentrated under reduced pressure to give a yellow solid, m.p. 74°–78°. This solid was partially dissolved in a mixture of 60 ml of hot ether and 15 ml of ethyl acetate, the mixture charcoaled, filtered and stripped to give a white solid, which was recrystallized from ether-pentane to give 3, as a white solid, m.p. 75°–77°.

EXAMPLE 4 —
2-(bromofluoronitromethyl)-5,6-dihydro-4H-1,3-thiazine (4)

46 g of perchloryl fluoride was bubbled into a solution/suspension of 12 g of 2A in 150 ml of pyridine at 0°–10° over a 2-hour-period. The mixture then was stirred at the same temperature for an additional 30 minutes, then concentrated under reduced pressure. The residue was dissolved in chloroform and washed successively with 25% acetic acid, saturated sodium bicarbonate solution, and saturated sodium chloride solution. The washed solution was dried ($Na_2SO_4$), then was stripped of solvent under reduced pressure to give a red liquid, sensitive to warmth. Chromatography of the liquid in silica gel using chloroform as eluent gave 4 as a pale yellow liquid.

2-(chlorofluoronitromethyl)-5,6-dihydro-4H-1,3-thiazine can be prepared in a similar manner, from 2-(chloronitromethylene)-tetrahydro-2H-1,3-thiazine [I] which can be prepared by stirring a mixture of 16.0 g of 1A and 13.4 g of N-chlorosuccinimide in 250 ml of carbon tetrachloride for an extended period at room temperature. I is recovered by filtering the crude reaction mixture, extracting the solid with methylene chloride, washing and drying the organic liquid phase, concentrating the solution under reduced pressure, and chromatographing the product on silica gel with a 1:1 methylene chloride/ethyl acetate mixture as eluent, I being a yellow solid, m.p.: 140°–141°.

Compounds of this invention exhibit useful insecticidal activity, being of particular interest for control of the larvae "caterpillar" or "worm" forms of insects of the genus Heliothis, such as *H. zea* (corn earworm, cotton bollworm, tomato fruitworm), *H. virescens* (tobacco budworm) and the genus Agrotis, such as *A. ipsilon* (black cutworm). Some are also of interest for controlling whiteflies, houseflies and pea aphids. In tests that have been conducted they have exhibited to toxicity to the two-spotted spider mite and some toxicity to mosquito larvae. Some act very rapidly, providing "quick knock-down" of insects: in some cases though the compound is not very toxic to the insects.

Activity of compounds of this invention with respect to insects was determined by using standardized test methods to establish the $LC_{50}$ dosage (in milligrams of test compound per 100 milliliters of solvent or liquid carrier required in the solution or suspension of test compound used) to kill 50% of the test insects. The test insects were the housefly, corn earworm, mosquito, pea aphid and 2-spotted spider mite.

All of compounds 1 through 4 were very active with respect to the corn earworm, and had low to moderate activity with respect to the pea aphid and housefly. Compounds 1, 2 and 3 had low activity with respect to mosquito larvae. None was active with respect to the pea aphid.

In the course of these tests it was noted that compounds 1 acted very quickly on houseflies and corn earworms, and compounds 2, 3 and 4 acted very quickly upon pea aphids.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material, which may be inorganic or organic and of synthetic or natural origin, with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, kaolinites, montmorillonites and micas; calcium carbonate; calcium sulfate; synthetic hydrated silicon oxides and synthetic clacium or aluminum silicates; elements such as for example, carbon and sulfur; natural and synthetic resins such as, for example, coumarone resins, polyvinyl chloride and styrene polymers and copolymers; solid polychlorophenols, bitumen, waxes such as beeswax, paraffin wax, and chlorinated mineral waxes; degradable organic solids, such as ground corn cobs and walnut shells; and solid fertilizers, for example, super-phosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0–10%w of additivies such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e. the dosage to which the insect contacts — is of the order of 0.001% to 0.5% based on the total weight of the formulation, though under some circumstances the effective concentration will be as little as 0.0001% or as much as 2%, on the same basis.

I claim as my invention:

1. A compound of the formula $$\text{hal}-\underset{\text{hal}'}{\overset{}{C}}-NO_2$$

(attached to a thiazine/thiazoline ring containing S and N)

wherein hal represents chlorine, bromine or fluorine, and hal' represents chlorine or bromine.

2. A compound according to claim 1 wherein hal and hal' each is bromine.

* * * * *